United States Patent [19]
Brunty

[11] Patent Number: 5,403,002
[45] Date of Patent: Apr. 4, 1995

[54] THROWING ARM TRAINING DEVICE

[76] Inventor: Steven H. Brunty, Rte. 1, Box 606, Chesapeake, Ohio 45619

[21] Appl. No.: 62,553

[22] Filed: May 18, 1993

Related U.S. Application Data

[63] Continuation-in-part of Ser. No. 717,325, Jun. 18, 1991, Pat. No. 5,222,733.

[51] Int. Cl.6 .............................................. A63B 67/00
[52] U.S. Cl. ...................................................... 273/55 R
[58] Field of Search ................ 273/55 R, 26 C, 26 R, 273/29 A; 128/80 B, 80 F, 80 C, 88, 80 R

[56] References Cited

U.S. PATENT DOCUMENTS

| | | |
|---|---|---|
| 1,772,601 | 8/1930 | Dunham . |
| 3,074,723 | 1/1963 | Esty ............................... 273/189 |
| 3,439,673 | 4/1969 | Sprecher ........................ 128/133 |
| 4,088,130 | 5/1978 | Applegate ..................... 128/80 F |
| 4,191,373 | 3/1980 | Lancellotti ..................... 128/77 |
| 4,254,953 | 3/1981 | Marchetti ...................... 128/77 |
| 4,372,298 | 2/1983 | Lerman ......................... 128/88 |
| 4,489,716 | 12/1984 | Blackwood et al. .......... 128/77 |
| 4,493,316 | 1/1985 | Reed et al. .................... 128/88 |
| 4,605,227 | 8/1986 | Hurd et al. ................... 273/189 A |
| 4,633,867 | 1/1987 | Kausek et al. ................ 128/88 |
| 4,657,000 | 4/1987 | Hepburn ....................... 128/88 |
| 4,726,361 | 2/1988 | Farley ........................... 128/80 B |
| 4,732,143 | 3/1988 | Kausek et al. ................ 128/88 |
| 4,875,677 | 10/1989 | Tetreault ...................... 128/77 |
| 4,884,561 | 12/1989 | Letson, Jr. ..................... 128/77 |
| 4,984,789 | 12/1989 | Socci ............................. 273/26 C |
| 5,062,858 | 11/1991 | Broeck et al. ................. 128/80 F |

Primary Examiner—Theatrice Brown
Attorney, Agent, or Firm—Richard C. Litman

[57] ABSTRACT

A throwing arm training device is attached to the user's arm to limit the flexion angle of the throwing arm to a maximum angle of 90 degrees or more and also the angle of extension to a desired minimum angle, thereby, encouraging maximum use of the latissimus dorsi muscle while discouraging sidearm throwing. The device comprises an upper arm and a forearm cuff having bars extending therefrom pivotally connected in the vicinity of the elbow by pivot screws mounted on a plate and connected to a limit plate having two arcuate slots centered on the pivot screws. Limit screws are slidably and lockably mounted in the slots to engage and limit the pivoting of the bars, and of the cuffs. The cuffs are attached to the arms by straps having Velcro fasteners, and include cushioning liners therein. The preferred materials for forming the straps include polypropylene, polyethylene, and copolymers of polypropylene and polyethylene. The device may be used by football quarterbacks and baseball pitchers to teach them the proper way to throw by maximizing shoulder use or movement in the throwing motion which results in an increase in the distance thrown. In a second and third embodiment, the maximum flexion angle may be set at least as high as 120 degrees and the minimum extension angle may be set at least as low as zero degrees, enabling a user's arm to travel through a range of at least 120 degrees between a maximum flexion angle and a minimum extension angle.

10 Claims, 3 Drawing Sheets

THROWING ARM TRAINING DEVICE

CROSS-REFERENCE TO RELATED APPLICATION

This application is a continuation-in-part of application Ser. No. 07/717,325, filed Jun. 18, 1991, (U.S. Pat. No. 5,222,733).

BACKGROUND OF THE INVENTION

1. Field of the Invention

This invention relates to a throwing arm training device used to teach individuals how to throw a football or baseball properly using the correct arm and elbow action.

Football quarterbacks and baseball pitchers have all too often suffered injury to their throwing arms because they did not use the correct arm and elbow action when throwing the football or baseball. The training device of this invention will help correct this problem.

The first major function of the throwing arm training device is to restrict the passer from throwing with the arm flexed inward toward the ear past a 90 degree angle mark shown on the training device. This automatically enables the thrower to maximize shoulder use or movement in the throwing motion which results in an increase in distance thrown. The major concern is that many throwers release the ball too close to the ear (inward past the 90 degree angle), resulting in increased rotation or spin on the ball and a decrease in the distance the ball is thrown.

The second major function of the throwing arm training device is that it also restricts the passer or pitcher from releasing a football or baseball with an overextended or fully extended arm both of which are better known as the "sidearm" method. The adverse effects of the sidearm method include poor accuracy, lack of distance, and added stress placed on the muscles of both the arm and the shoulder.

Both angles on the throwing arm training device are adjustable, However, the recommended adjustment limiting the flexion of the arm should be set at the 90 degree angle. The angle of extension should be adjusted according to the severity of the sidearm problem, For example, with one having sidearm throwing problems, a coach might lock the extension adjustment at the 80 degree angle and have the subject practice throwing with the throwing arm training device on a daily basis, so that the subject will learn to effectively release the ball between the 80 degree and 90 degree angle. When the thrower and/or his or her coach decides that he or she is now comfortable with the newly formed throwing motion, the extension angle can be gradually let out or decreased over a period of time until the thrower can perform the proper throwing motion without the extension restriction. At that time, the device can be removed from the arm and a new improved throwing motion should have evolved. Now the thrower will be able to throw a football or baseball using the proper technique without the aid of the throwing arm training device.

In the second and third embodiments of the invention the maximum flexion angle may be set at an angle higher then 90 degrees, while the minimum extension angle in all three of the embodiments may be set as low as zero degrees if desired. Such modified adjustments are necessary for individuals who do not have a problem with sidearm throwing and/or throwing the ball close to the ear.

2. Description of the Prior Art

Arm control devices for both behavior modification and training are well known in the prior art, U.S. Pat. No. 1,772,601 issued Aug. 12, 1930, to Berman S. Dunham discloses a thumb-sucking preventing device comprising a pair of sleeves or cuffs mountable on an arm above and below the elbow, respectively, said pair of sleeves or cuffs being pivotally connected in the vicinity of the elbow by two rotatable plates, the pivotal movement being limited by a pin and slot connection.

U.S. Pat. No. 3,074,723 issued Jan. 22, 1963, to Clement Esty discloses a golfing practice aid which comprises a sleeve or cuff which is mounted on a golfer's forearm and elbow of his leading arm to remind the golfer to keep his or her leading arm straight during the course of his or her backswing, U.S. Pat. No. 3,439,673 issued Apr. 22, 1969, to Carl A. Sprecher discloses an elbow immobilizer for use on male and female patients to facilitate intravenous administration of food, blood, or other fluids, comprising a pair of elongated support members of sufficient length to prevent a person from bending his arm, said support members being attached to the arm by a pair of straps above and below the elbow, and a third intermediate strap at the elbow.

U.S. Pat. No. 4,875,677 issued Oct. 24, 1989, to Albert G. Tetreault discloses a training aid for baseball hitters to assist in keeping a batter's lead arm flexed in a proper hitting stance, comprising a first sleeve or cuff attached to the batter's upper arm, a second sleeve connected to the forearm and one or more elastic straps connected between the two cuffs.

U.S. Pat. No. 4,984,789 issued Jan. 15, 1991, to Roger D. Socci, discloses a device to help teach and train baseball pitchers to use the correct arm and elbow action when pitching a baseball, comprising an arm elevator harness which fits around the pitcher's body, and an arm and elbow elevator guide which is attached to the shoulder harness and guides the pitcher's pitching arm in the right position.

Additionally, the following patents were cited in my pending patent application Ser. No. 07/717,325: U.S. Pat. No. 4,088,130 issued May 9, 1978, to Leslie T. Applegate; U.S. Pat. No. 4,191,373 issued Mar. 4, 1980, to William E. Lancellotti; U.S. Pat. No. 4,254,953 issued Mar. 10, 1981 to Ralph D. Marchetti; U.S. Pat. No. 4,372,298 issued Feb. 8, 1983 to Max Letman; U.S. Pat. No. 4,489,716 issued Dec. 25, 1984 to Robert L. Blackwood and David M. Shapiro; U.S. Pat. No. 4,493,316 issued Jan. 15, 1985 to Kenneth E. Reed et al.; U.S. Pat. No. 4,605,227 issued Aug. 12, 1986 to Bruce Hurd et al.; U.S. Pat. No. 4,633,867 issued Jan. 6, 1987 to James H. Kausek et al.; U.S. Pat. No. 4,726,361 issued Feb. 23, 1988 to Michael D. Farley; U.S. Pat. No. 4,657,000 issued Apr. 14, 1987 to George R. Hepburn; U.S. Pat. No. 4,732,143 issued Mar. 22, 1988 to James H. Kausek et al.; U.S. Pat. No. 4,884,561 issued Dec. 5, 1989 to Billy R. Letson, St.; and U.S. Pat. No. 5,062,858 issued Nov. 5, 1991 to Vanden Broeck et al. Of these Patents, the Patent to Applegate discloses a hinge for a knee brace comprising a single pivot connecting two bars, enabling pivotal movement between selected fixed positions determined by the positions of pins placed in a series of apertures. The Patent to Lancellotti discloses a brace adapted for wear by a tennis player for minimizing and/or preventing tennis elbow comprising a means 24, 38 for applying pressure to those portions of a tennis player's arm directly overlying the medial and lateral epicondyles, thereby preventing or reducing the pulling action of the tendon connections with these bone spurs in such a manner that the inflammation thereof are reduced. Marchetti discloses an elbow movement restrictor which is adapted to hold an arm of a golfer or bowler in an extended locked position, thereby restricting the "breaking" of the player's elbow on making the bowling delivery or completing the golf stroke, the two operative bars 20 and 22 being connected by a single pivot screw 28, bar 20 being locked in the extended position by means of screw 30 and depression 32. The Patent to Lerman discloses a knee brace to provide exterior support to the knee to prevent any unnatural movements of the knee joint which could injure or reinjure the knee ligaments, while allowing the normal swinging movement of the knee joint about a horizontal axis through the knee. The Patent to Blackwood et al. discloses a hypertension limiting elbow brace designed to hold a person's arm in a partially bent attitude. The Patent to Reed et al. is directed to an articulating knee stabilizer. The limits on free rotation of the hinge is provided by pinion stop gears 61 and 63 which engage hinge gears 56 and 58 until they engage the teeth of an opposite hinge gear, thus preventing further rotation of the hinge. The Patent to Hurd et al. is directed to an athlete's arm restrainer, for holding a bowler's arm rigid after it is straightened. The Patent to Kausek et al. '867 is directed to a knee brace for control of ligament instability by protecting against forces applied in the medial and lateral side planes and in the anterior and posterior planes, and providing rotational stability so as to prevent excessive rotation of the tibia in relation to the femur. The brace also inhibits pivot shift (forward displacement of the tibia) by preventing the knee from achieving a full extension by means of an extension check strap 30.

The Patent to Farley is directed to a method and apparatus for correction of various defects in an equine leg, including a brace attached to an animal's leg in three places. A pad is provided for engaging a deviated joint and pulling the joint against a side of the brace to correct the deviation. Adjacent sections are connected by pivotal elements arranged to provide movement of the three brace sections in a common plane or parallel planes so that the device, in essence, establishes a reference direction for movement of the parts of the leg. Because the apparatus provides pivotal connection the horse is allowed to walk about, does not view the apparatus as a foreign object, and does not injure itself trying to get away from the apparatus. The apparatus is also useful for treatment of contractures because the preferred pivotal elements include limiting stops for controlling the angular motions of the brace. The lower connector 12 is designed to permit rotation of section 8 in a counter-clockwise direction when viewed in FIG. 1 of the Patent, while the upper connector permits rotation of section 6 in a clockwise direction. The connectors operate in opposite directions to accommodate the action of an animal's leg. To adapt the Farley device to a human arm would require substantial modification.

The Patent to Hepburn is directed to an adjustable splint and securing means therefor, incorporates a biasing spring therein to constantly bias the working elements into a fully extended position. The Patent to Kausek et al. '143 discloses a selectable extension stop for a polycentric hinge comprising an extension block positionable between mating ends of arms to limit the forward rotation of the arms, different size blocks being required to enable the user to select the limit of extension. The Patent to Letson, Sr. discloses an articulated brace for protection of the joint of a wearer's limbs, comprising three sections mounted on a single pivot to provide protection of the joint, with a stop 34 engageable with a surface 40 being provided to limit the pivotal movement of the brace in a direction that would allow for hyperextension of the limbs.

Not found in the prior art is a throwing arm training device wherein the maximum flexion angle of the arm and the minimum extension angle can be selectively set to provide a user with a range of arm movement within limits for the purpose of training the user to throw a ball such as a football so as to achieve the maximum benefit in terms of height and distance,

SUMMARY AND OBJECT OF THE INVENTION

It is an object of this invention to provide a throwing arm training device for football quarterbacks and baseball pitchers which avoids the defects of prior art training devices.

It is a further object of this invention to provide a throwing arm training device which adjustably limits the flexion angle and the extension angle of a throwing arm.

The throwing arm training device comprises a U-shaped sleeve or cuff for the upper arm and a U-shaped sleeve or cuff for the forearm. The cuffs may be formed of a relatively stiff plastic material such as polypropylene, a less rigid plastic material such as polyethylene, or a copolymer of polypropylene and polyethylene.

Provided within the cuffs is a liner formed of any conventional cushioning material. The cuffs are joined together on either side by a pair of bars, each pair having mating gear teeth at one end held in an engageable position by pivots mounted on a pivot support plate which in turn is connected to a metal limit guide and support plate by the pivots. The limit devices comprise screws and nuts adjustably mounted in slots provided in the limit guide and support plate. The limit screws may be tightened or loosened by means of an allen wrench. By adjusting the limit screws, the angle of flexion and the angle of extension may be set. If found to be desirable, a screw may be added to the pivot plate to provide a sturdier and stronger connection. The cuffs are attached to and held onto a thrower's arm by means of flexible straps having Velcro fastening means, the straps being passed through cooperating loops.

A foam rubber cushion may be provided on the inner surface of the limit guide and support plate to protect the elbow from chafing, as shown in FIG. 3.

In the first embodiment, shown in FIGS. 1-3 and claimed in parent application Ser. No. 07/717,325 filed Jun. 18, 1991, the angle of flexion is preferably set at 90 degrees and the angle of extension is set between approximately 60 degrees and 90 degrees depending on the severity of a sidearm throwing problem. It has been found that some quarterbacks, for example, may not have a problem throwing the ball in a shotput fashion but may have a problem throwing the ball in sidearm fashion, or vice versa. Therefore, it is desirable to be able to adjust the angle of flexion limit above 90 degrees and the angle of extension limit below 60 degrees. The arrangement disclosed in FIGS. 4 and 5 enable adjustment between 0 degrees and approximately 120 degrees, thereby covering the full range of adjustment that might be needed for any one individual.

Other objects, features, and advantages of this invention will become apparent from the following detailed description and the appended claims, reference being had to the accompanying drawings forming a part of the specification, wherein like reference numerals designate corresponding parts of the several views.

DETAILED DESCRIPTION OF THE PREFERRED EMBODIMENTS

Before explaining in detail the present invention, it is to be understood that the invention is not limited in its application to the details of construction and arrangement of parts illustrated in the accompanying drawing, since the invention is capable of other embodiments and of being practiced or carried out in various ways. Also, it is to be understood that the phraseology and terminology employed herein is for the purpose of description and not limitation.

Figure 1:
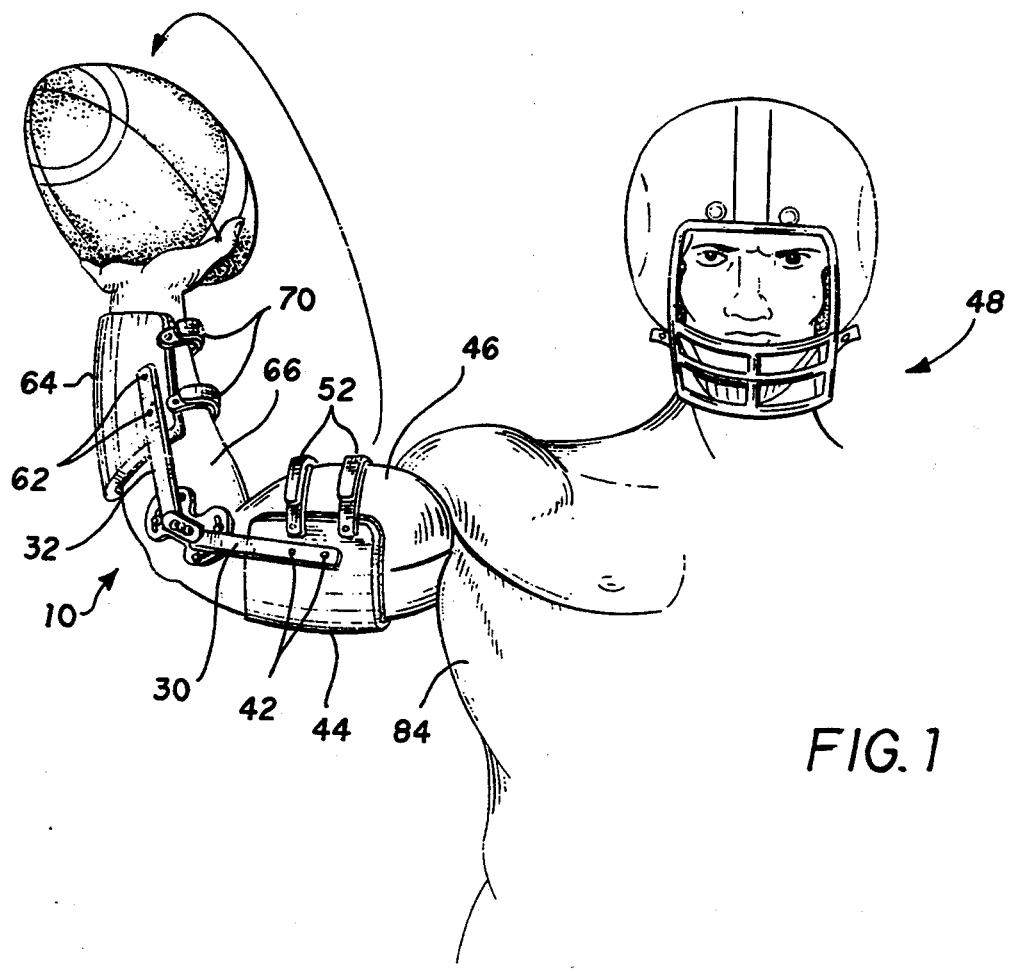
FIG. 1 is a perspective view showing the throwing arm training device in use.
Figure 2:
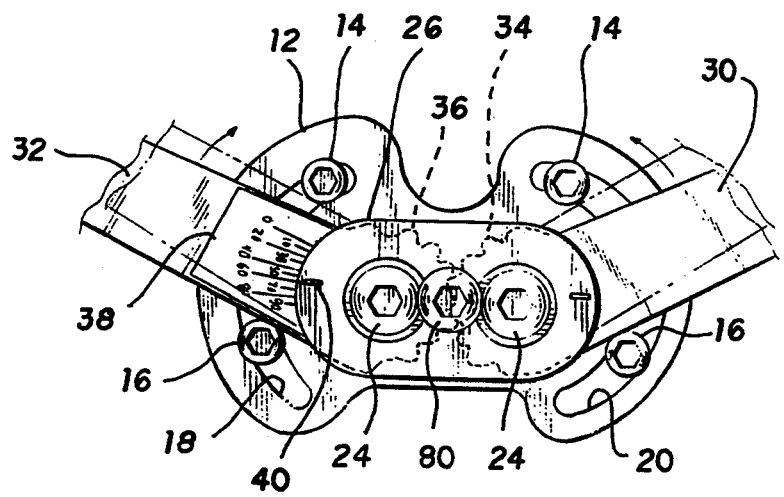
FIG. 2 is a plan view showing the pivoting and limiting devices of the throwing arm training device.

FIG. 1 is a perspective view showing the throwing arm training device 10 in use. As shown in FIG. 2, the limit guide and support plate 12 limits the flexion angle of the forearm to 90 degrees by the placement of Lipper limit screws 14. Upper limit screws 14 and lower limit screws 16 are slidably adjustable along arcuate slots 18 and 20 and are locked in position by means of nuts 22. The radial centers of arcuate slots 18 and 20 are respectively located at the axis of left and right pivot screws 24.

Limit guide and support plate 12 also supports left and right pivot screws 24 which pass through openings (not shown) in pivot support plate 26 and which are screwed into threaded holes 28 in limit guide and support plate 12.

Pivotally mounted on pivot screws 24 between limit guide and support plate 12 and pivot support plate 26 are a first bar 30 and a second bar 32 having cooperating gear teeth 34 and 3G. Because of the cooperating gear teeth rotation of one bar 30 or 32 about its pivot screw 24, will cause a corresponding equal and opposite rotation of the other bar 32 or 30 about its pivot screw 24, the degree of rotation being limited by upper and lower limit screws and 16. Attached to second bar 32 is a scale 38 which, cooperating with mark 40, identifies the degree of rotation of bars 30 and 32. Bar 30 is connected by rivets 42 to a U-shaped sleeve or cuff 44 configured to fit the upper arm 46 of the user 48. Cuff 44 includes a liner 50, straps 52 attached to cuff 44 by rivets 54, and loops 56 attached to cuff 44 by rivets 58. Straps 52 include Velcro fastening means 60 whereby cuff 44 may be secured to upper arm 46 as shown in FIG. 1.

8at 32 is attached by rivets 62 to U-shaped sleeve or cuff 64 configured to fit forearm 66 of user 48. Cuff 64 includes a liner 68, straps 70 attached by rivets 72 to cuff 64, and loops 74 attached to cuff 64 by rivets 76. Straps 70 include Velcro fastening means 78 whereby cuff 64 may be secured to forearm 66 as shown in FIG. 1.

Figure 3:
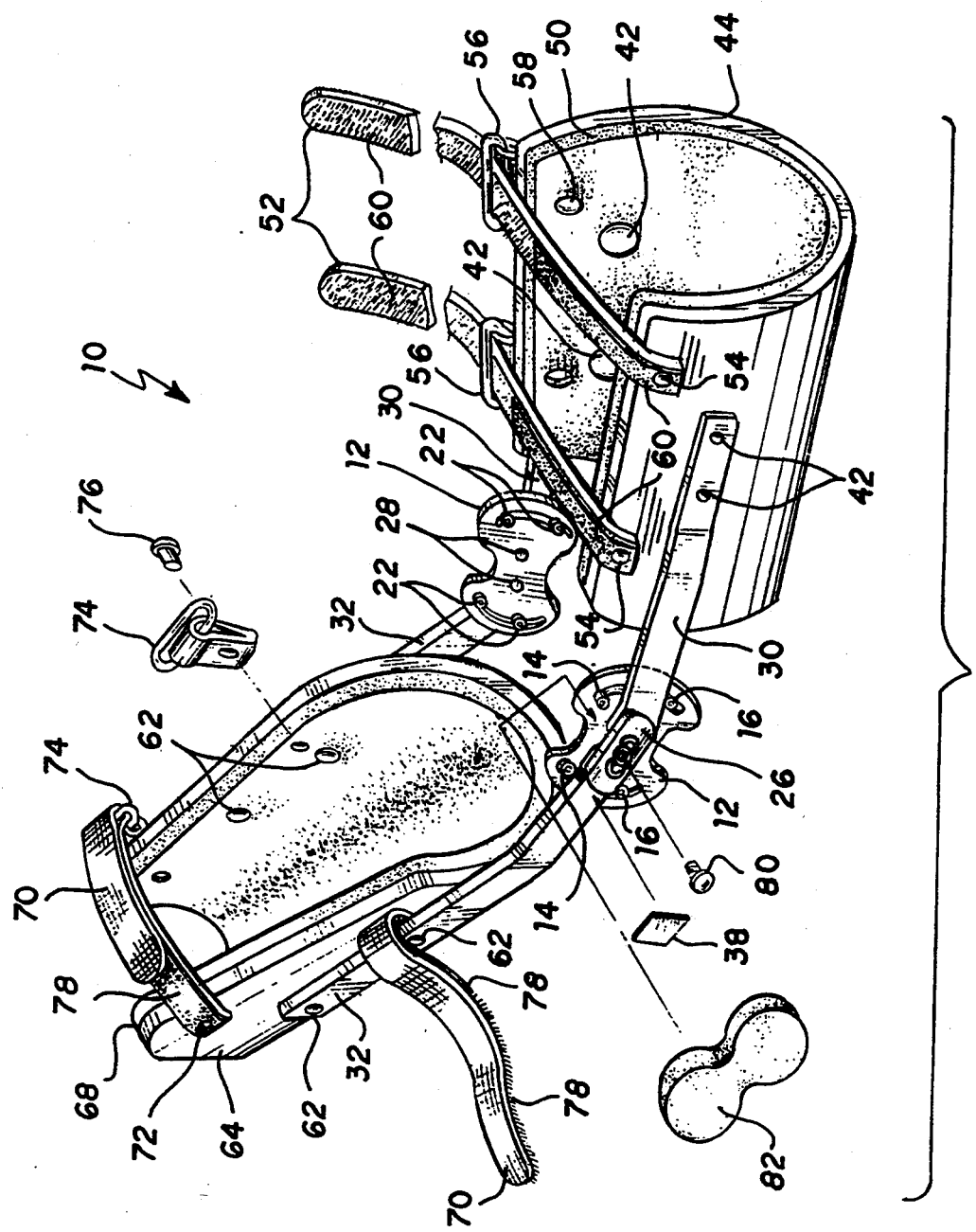
FIG. 3 is an exploded perspective view of the throwing arm training device showing how the several components cooperate and/or FIG. 4 is a plan view similar to FIG. 2 showing a second embodiment of the pivoting and limiting devices of the throwing arm training device.

Elements 12, 14, 16, 18, 20, 22, 24, 26, 28, 30, 32, 34, 36, 38, 40 and 42 located along the inner side of the arm 46, 66 in FIGS. 1, 2 and 3 are duplicated on the outer side of the arm as shown in FIG. 3. As shown in FIGS. 2 and 3, a screw 80 may be added to pivot support plate 26, the head of screw 80 bearing on pivot screws 24 to provide stability therefor. In the event that limit guide and support plates 12 and nuts 22 carried by plates 12 rub against the user's elbow, a piece of sponge rubber 82 may be glued to the inner side of plates 12.

Plates 12 and 26 and bars 30 and 32 are formed of metal, such as aluminum or steel. Cuffs 44 and 64 are formed of plastic material which is fairly rigid, such as polypropylene. As an alternative, softer cuffs may be formed of polyethylene or a copolymer of polypropylene and polyethylene. In the preferred embodiment, the plastic material is approximately ⅛ inch thick. The liner 50, 68 is formed of any conventional cushioning material. The thickness of the liner 50, 68 can vary in 1/16 inch increments, from ⅛ inch to ¾ inch. Because of the variance in arm sizes, it is contemplated that the cuffs 44, 64 will be made in at least three different sizes.

In use, upper limit screws 14 may be set at 90 degrees in slots 18 and 20, and if desired, such a setting may be considered as being permanent. This setting restricts the passer from throwing with the arm flexed inward towards the ear past the 90 degree angle mark shown, which forces the thrower to maximize the use of rotation of the shoulder during the throwing motion taking away from the stress on the elbow while at the same time the latissimus dorsi muscle (84, FIG. 1) plays a major role in powering the throw.

Lower limit screws 16 determine the angle of extension, which is adjusted according to the severity of the sidearm problem. As set in FIG. 2, the arm may extend over a range of 30 degrees, from 90 degrees to 60 degrees. Ideally, the throwing motion ends with an exaggerated snapping of the wrist. During a training period, lower limit screws 16 may be set at any position desired by the thrower and/or his or her coach.

Figure 4:
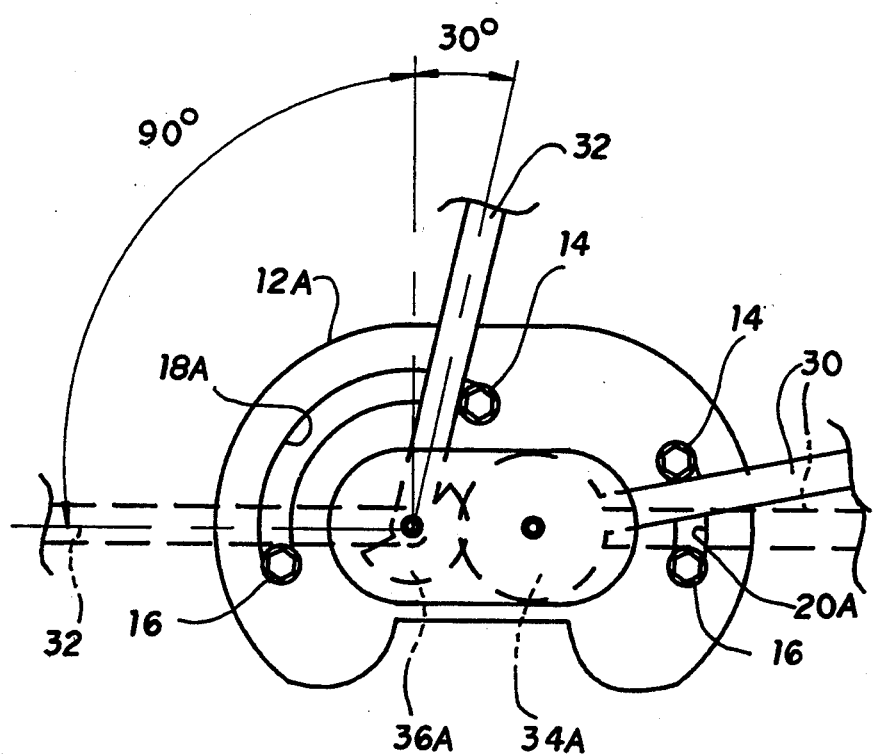

As shown in FIG. 2, the extension angle could be set as low as 0 degrees enabling the arm 4G, 6G of user 48 to be fully extended by setting lower limit screws at the bottom of slots 18 and 20 in limit guide and support plate 12. In FIG. 4, there is shown a modification of the limit guide and support plate identified by reference numeral 12A in which slots 18A and 20A having a radius extending to pivot screws 24 have been extended at the top of limit guide and support plate 12A to enable the flexion angle to be set higher than 90 degrees by suitable positioning of the upper limit screws in slots 18A and 20A. As shown in FIG. 4, the flexion angle could be set as high as 120 degrees, although other limits may be selected if found to be desirable. A scale similar to scale 38 in FIG. 2 may be placed on bar 32 to indicate the range of settings available, depending on the length of slots 18A and 20A, and the selective partitioning of upper and lower limit screws 14 and 16. Depending on the degree of rotation desired the cooperating gears may be the same size as represented by gear teeth 34 and 36 in FIG. 2, or of different diameters as shown in FIG. 4.

Figure 5:
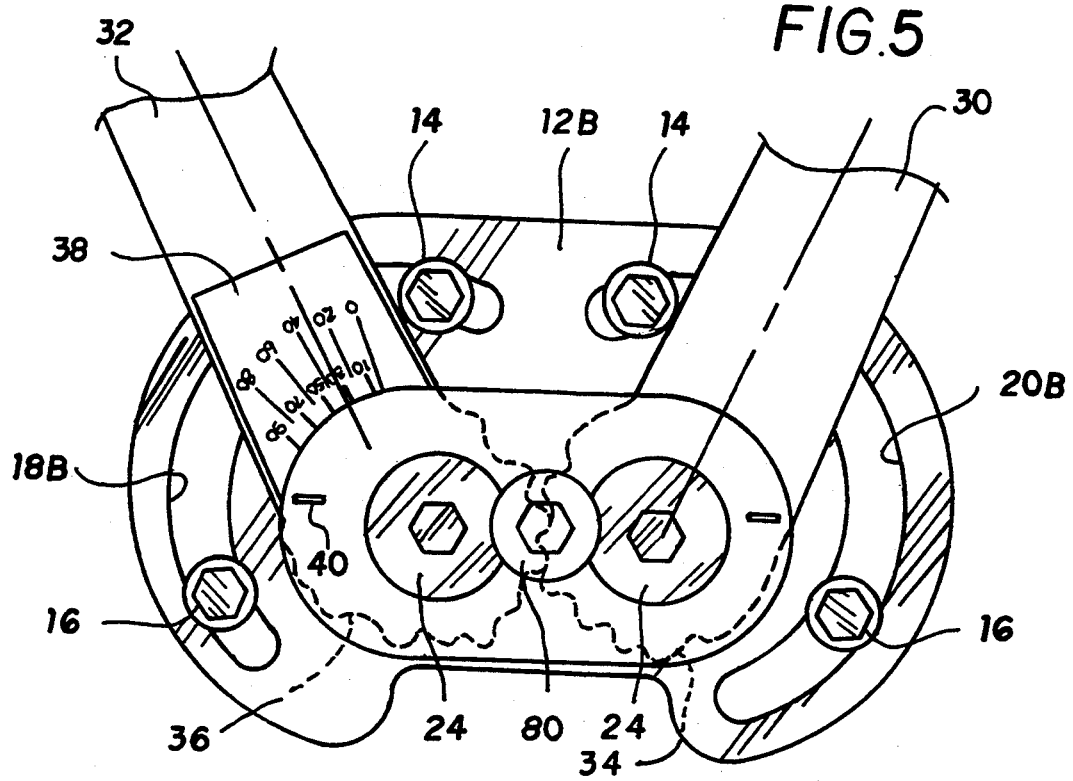
FIG. 5 is a plan view similar to FIG. 2 showing a third embodiment of the pivoting and limiting devices of the throwing arm training device.

In the embodiment of FIG. 5, similar to FIG. 2, the 120 degrees of movement is divided equally between the upper arm and the forearm, by equally extending arcuate slots 18B and 20B in limit guide and support plate 12B. The cooperation and/or coaction between the several elements shown in FIG. 5 is the same as in FIG. 2.

With a selectable range between 0 degrees and 120 degrees, by way of example only, the throwing arm training device can be used to correct a number of different throwing problems.

While it will be apparent that the preferred embodiment of the invention herein disclosed is well calculated to fulfill the objects above-stated, it will be appreciated that the invention is susceptible to modification, variation and change without departing from the proper scope or fair meaning of the subjoined claims.

I claim:

1. A throwing arm training device comprising:
    a U-shaped upper arm cuff means including cushioning liner means on an inner surface thereof, strap means having fastening means thereon for fastening said U-shaped upper arm cuff means to a user's upper arm, and first bar means connected to and extending from each side of said U-shaped upper arm cuff means;
    a separate U-shaped forearm cuff means including cushioning liner means on an inner surface thereof, strap means having fastening means thereon for fastening said U-shaped forearm cuff means to said user's forearm, and second bar means connected to and extending from each side of said U-shaped forearm cuff means;
    a pivot support plate means aligned with said first and second bar means extending from each side of said U-shaped upper arm cuff means and said U-shaped forearm cuff means, each said pivot support plate means including a first pivot screw means, and a second pivot screw means, said first and second bar means on each side of said upper arm cuff means and said forearm cuff means being pivotally mounted on said first and second pivot screw means, respectively;
    said first and second bar means having intermeshing gear teeth at the pivoted ends on each side of said respective cuff means to ensure controlled pivoting thereof;
    a limit guide and support plate means connected to said first and second pivot screw means on the side of said first and second bar means opposite said pivot support plate means to thereby sandwich said first and second bar means between said pivot support plate means and said limit guide and support plate means on each side of said respective cuff means, at least one of said first and second bar means having scale indicia on a surface thereof and a corresponding indicia mark placed on a pivot plate of said pivot plate means whereby a desired maximum angle of extension may be identified;
    cushion means attached to a surface of said limit guide and support plate means for protection of the elbow of a person when in use;
    each said limit guide and support plate means having a first arcuate slot means and a second arcuate slot means, the radial centers thereof being located at the corresponding first and second pivot screw means;
    upper limit screw means adjustably and lockably located at one end of said first and second arcuate slot means engageable with upper edges of said first and second bar means on each side of said respective cuff means to limit the maximum flexion angle of a user's arm; and
    lower limit screw means adjustably and lockably located in said first and second arcuate slot means and engageable with lower edges of said first and second bar means on each side of said respective cuff means to limit the degree of extension of the forearm of the user relative to the upper arm during the act of throwing; whereby
    the user is restricted from the throwing with the forearm flexed towards a user's ear beyond a selected maximum flexion angle, and is further restricted from releasing a ball with an over-extended arm, while encouraging the maximum use of the latissimus dorsi muscle to rotate the user's arm during the act of throwing.

2. A throwing arm training device as in claim 1, wherein said fastening means for said upper arm cuff means and for said forearm cuff means comprise hook and loop fasteners.

3. A throwing arm training device as in claim 1, said upper arm cuff means and said forearm cuff means being formed of plastic material selected from the group consisting of polypropylene, polyethylene, and copolymers thereof.

4. A throwing arm training device as in claim 1, further including a stabilizing screw centrally located on each said pivot support plate means and bearing on said pivot screw means.

5. A throwing arm training device as in claim 1, wherein said first arcuate slot means and said second arcuate slot means have a length sufficient to enable a range of movement between the maximum flexion angle and the minimum extension angle of at least 90 degrees.

6. A throwing arm training device as in claim 1, wherein said first arcuate slot means and said second arcuate slot means have a length sufficient to enable a range of movement between the maximum flexion angle and the minimum extension angle of at least 120 degrees.

7. A throwing arm training device as in claim 1, wherein said first arcuate slot means and said second arcuate slot means have a length sufficient to enable the maximum flexion angle to be selectively set at least to a maximum of 90 degrees.

8. A throwing arm training device as in claim 1, wherein said first arcuate slot means and said second arcuate slot means have a length sufficient to enable the maximum flexion angle to be selectively set at least to a maximum of 120 degrees.

9. A throwing arm training device as in claim 1, wherein said first arcuate slot means and said second arcuate slot means have a length sufficient to enable the minimum extension angle to be selectively set at least to zero degrees.

10. A throwing arm training device as in claim 1, wherein said intermeshing gear teeth have the same pitch on variably sized cooperating gear sections, whereby said first and second bar means travel through different angles between the selected maximum angle of flexion and minimum angle of extension.

* * * * *